United States Patent
Makeiff et al.

(10) Patent No.: US 9,067,878 B2
(45) Date of Patent: *Jun. 30, 2015

(54) ORGANOGEL COMPOSITIONS COMPRISING ALKYLATED AROMATIC ACIDS

(75) Inventors: Darren A. Makeiff, St. Albert (CA); Rina Carlini, Oakville (CA)

(73) Assignee: Xerox Corporation, Norwalk, CT (US)

( * ) Notice: Subject to any disclaimer, the term of this patent is extended or adjusted under 35 U.S.C. 154(b) by 355 days.

This patent is subject to a terminal disclaimer.

(21) Appl. No.: 13/327,655

(22) Filed: Dec. 15, 2011

(65) Prior Publication Data
US 2013/0158135 A1    Jun. 20, 2013

(51) Int. Cl.
| | | |
|---|---|---|
| C07F 5/02 | (2006.01) | |
| C07C 63/04 | (2006.01) | |
| C07C 275/42 | (2006.01) | |
| C07C 233/54 | (2006.01) | |
| C07C 63/15 | (2006.01) | |

(52) U.S. Cl.
CPC ............... *C07C 63/04* (2013.01); *C07C 275/42* (2013.01); *C07C 233/54* (2013.01); *C07C 63/15* (2013.01)

(58) Field of Classification Search
None
See application file for complete search history.

(56) References Cited

U.S. PATENT DOCUMENTS

| | | | | |
|---|---|---|---|---|
| 6,506,853 | B2 * | 1/2003 | Duan | 525/444 |
| 7,503,973 | B1 * | 3/2009 | Carlini | 106/496 |
| 7,883,574 | B2 | 2/2011 | Carlini et al. | |
| 7,905,954 | B2 | 3/2011 | Carlini et al. | |
| 2002/0019430 | A1* | 2/2002 | Jackson et al. | 514/406 |
| 2010/0037955 | A1 | 2/2010 | Carlini et al. | |

OTHER PUBLICATIONS

Hoefnagel et al., Journal of the Chemical Society, Perkin Transactions 2: Physical Organic Chemistry (1972-1999) (1989), (8), 977-86.*
Database Caplus Chemical Abstracts Service, Columbus, Ohio, US; Database Accession No. 2010:1602203, Abstract of U.S. 7,503,973, Carlini et al., Xerox Corporation, USA, Mar. 17, 2009.*
Database Caplus Chemical Abstracts Service, Columbus, Ohio, US; Database Accession No. 2010:19955, Abstract of EP 2290013 to Xerox Corporation, USA; National Research Council of Canada.*
EP 2290013 via WIPO Patentscope.*
Zafar et al., Tet. Lett. 1996, 37, 14, 2327-2330.*
Lee et al., J. Am. Chem. Soc. 2007, 129, 1040-1041.*
Darren A. Makeiff et al., Copending U.S. Appl. No. 12/777,329, filed May 11, 2010.
Darren A. Makeiff et al., Copending U.S. Appl. No. 12/820,497, filed Jun. 22, 2010.
Raghavan, S. and Cipriano, B., "Gel Formation: Phase Diagrams Using Tabletop Rheology and Calorimetry", Chapter 8, pp. 241-252 in Molecular Gels, Weiss, R. and Terech, P., eds., Springer (2006).
Terech, P.; Weiss, R. G. Chem. Rev. 1997, 97, 3133-3159.
Hirst, A. R.; Escuder, B.; Miravet, J. F.; Smith, D. K. Angew. Chem. Int. Ed. 2008, 47, 8002-8018.
Lee, H. Y.; Nam, S. R.; Hong, J.—I. J. Am. Chem. Soc. 2007, 129, 1040-1041.
Nam, S. R.; Lee, H. Y.; Hong, J.—In. Tetrahedron 2008, 64, 10531-10537.
Potluri, V. K.; Hamilton, A. D. J. Supramol. Chem. 2002, 2, 321-326.
Zafar, A.; Yang, J.; Geib, S. J.; Hamilton, A. D. Tet. Lett. 1996, 37, 14, 2327-2330.
Rodriguez-Llansola, F.; Escuder, B.; Miravet, J. F.; Hermida-Merino, D.; Hamley, I. W.; Cardin, C. J.; Hayes, W. Chem. Commun. 2010, 7960-7962.
Hu, H.-Y.; Yang, Y.; Xiang, J.F.; Chen, C.-F. Chin. J. Chem. 2007, 25, 1389-1393.
Darren A. Makeiff et al., Copending U.S. Appl No (not yet assigned), filed concurrently herewith.
Darren A. Makeiff et al., Copending U.S. Appl. No. 13/293,963, filed Nov. 10, 2011.
Lebel, O.; Perron, M.-E.; Maris, T.; Zalzal, S. F.; Nanci, A.; Wuest, J. D. Chem. Mater. 2006, 18, 3616-3626.

* cited by examiner

*Primary Examiner* — Karl J Puttlitz
(74) *Attorney, Agent, or Firm* — MDIP LLC

(57) ABSTRACT

Disclosed is a composition comprising an organogel which comprises: (a) an alkylated aromatic acid compound of the formula

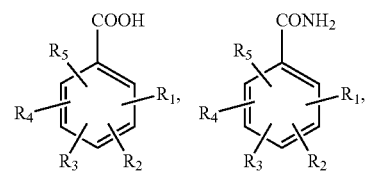

or mixtures thereof, wherein $R_1$, $R_2$, $R_3$, $R_4$, and $R_5$ each, independently of the other, are hydrogen, alkyl, aryl, arylalkyl, or alkyl, provided that at least one of $R_1$, $R_2$, $R_3$, $R_4$, and $R_5$ is —X—$R_c$, wherein —X— is a linking group between $R_c$ and the aromatic group and $R_c$ is alkyl; and (b) an organic liquid.

16 Claims, No Drawings

ORGANOGEL COMPOSITIONS COMPRISING ALKYLATED AROMATIC ACIDS

CROSS-REFERENCE TO RELATED APPLICATIONS

Reference is made to U.S. application Ser. No. 12/820,497, filed Jun. 22, 2010, entitled "Self-Assembled Nanostructures," with the named inventors Darren Makeiff and Rina Carlini, the disclosure of which is totally incorporated herein by reference.

Reference is made to Copending Application Ser. No. 13/327,664, filed concurrently herewith, entitled "Phase Selective Gelation With Alkylated Aromatic Acid Compounds," with the named inventors Darren A. Makeiff and Rina Carlini, the disclosure of which is totally incorporated herein by reference.

PARTIES TO A JOINT RESEARCH AGREEMENT

This application is a result of activities undertaken within the scope of a joint research agreement between Xerox Corporation and the National Research Council of Canada that was in effect on or before the date the research leading to this application was made.

BACKGROUND

Disclosed herein are organogel compositions comprising alkylated aromatic acid compounds and organic liquids.

The "bottom up" self-assembly of molecular building blocks into nanostructured materials has attracted significant interest for advanced materials research. Nanostructured materials with controlled size, shape, and function are important for numerous industrial applications. Low molecular weight organogels are a rapidly developing class of such materials, in which small molecular building blocks self-assemble into one-dimensional assemblies stabilized by manifold non-covalent interactions (i.e., hydrogen bonding, pi-stacking, van der Waals, metal-ligand, or the like, as well as combinations thereof) that can entangle and intertwine into three-dimensional networks at very low concentrations. Solvent molecules are entrapped within the interstices of the network, resulting in rigidification of the fluid, affecting the macroscopic flow behavior and properties of the bulk liquid. The use of organogel materials is diverse and rapidly developing, and spans many applications such as medicine, electronics, printing, personal care, and environmental remediation. Although a large number of organogelator compounds are known, the rational design and synthesis of new organogelators for specific liquids of interest for commercial applications remains a significant challenge since the gel properties in a given liquid cannot be predicted from the molecular structures alone. In addition, not all self-assembling nanostructures form gels when placed in contact with a liquid.

SUMMARY

Disclosed herein is a composition comprising an organogel which comprises: (a) an alkylated aromatic acid compound of the formula

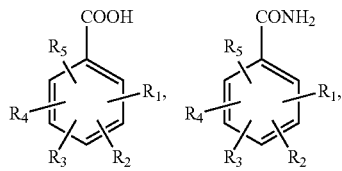

or mixtures thereof, wherein $R_1$, $R_2$, $R_3$, $R_4$, and $R_5$ each, independently of the other, are: (A) hydrogen atoms; (B) alkyl groups, including substituted and unsubstituted alkyl groups, wherein hetero atoms either may or may not be present in the alkyl group; (C) aryl groups, including substituted and unsubstituted aryl groups, wherein hetero atoms either may or may not be present in the aryl group; (D) arylalkyl groups, including substituted and unsubstituted arylalkyl groups, wherein hetero atoms either may or may not be present in either or both of the alkyl portion and the aryl portion of the arylalkyl group; or (E) alkylaryl groups, including substituted and unsubstituted alkylaryl groups, wherein hetero atoms either may or may not be present in either or both of the alkyl portion and the aryl portion of the alkylaryl group; provided that at least one of $R_1$, $R_2$, $R_3$, $R_4$, and $R_5$ is —X—$R_c$, wherein: (F) —X— is a linking group between $R_c$ and the aromatic group; and (G) $R_c$ is an alkyl group, including substituted and unsubstituted alkyl groups, wherein hetero atoms either may or may not be present in the alkyl group; with the provisos that: (1) when the compound is of the formula

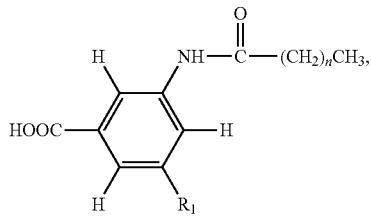

either $R_1$ is not

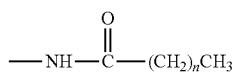

or n is not 9, 10, or 11; (2) when the compound is of the formula

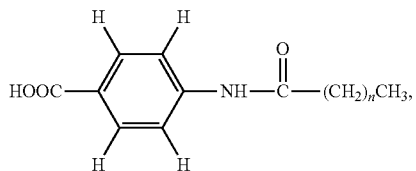

n is not 9, 10, or 11; (3) when the compound is of the formula

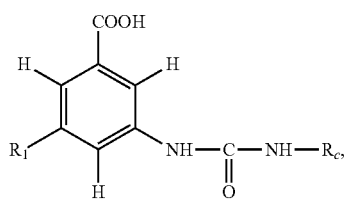

either R$_1$ is not —COOH or R$_c$ is not

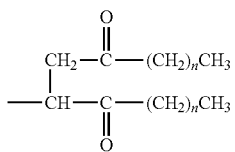

wherein n is 8 to 10; and (4) when the compound is of the formula

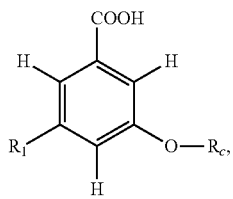

either R$_1$ is not —COOH or R$_c$ is not

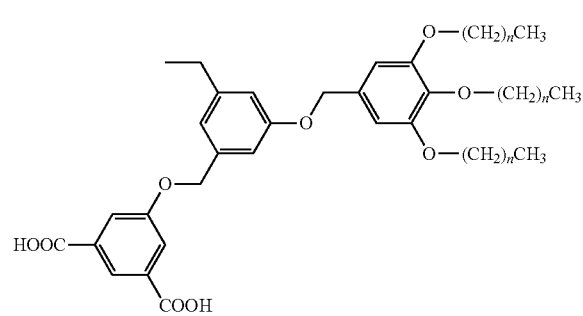

wherein n is from 8 to 10; and (b) an organic liquid. Also disclosed herein is a composition comprising an organogel which comprises: (a) an alkylated aromatic acid compound of the formula

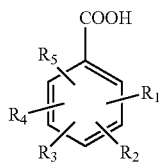

or mixtures thereof, wherein R$_1$, R$_2$, R$_3$, R$_4$, and R$_5$ each, independently of the other, are: (A) hydrogen atoms; (B) alkyl groups, including substituted and unsubstituted alkyl groups, wherein hetero atoms either may or may not be present in the alkyl group; (C) aryl groups, including substituted and unsubstituted aryl groups, wherein hetero atoms either may or may not be present in the aryl group; (D) arylalkyl groups, including substituted and unsubstituted arylalkyl groups, wherein hetero atoms either may or may not be present in either or both of the alkyl portion and the aryl portion of the arylalkyl group; or (E) alkylaryl groups, including substituted and unsubstituted alkylaryl groups, wherein hetero atoms either may or may not be present in either or both of the alkyl portion and the aryl portion of the alkylaryl group; provided that at least one of R$_1$, R$_2$, R$_3$, R$_4$, and R$_5$ is —X—R$_c$, wherein: (F) —X— is a linking group between R$_c$ and the aromatic group; and (G) R$_c$ is an alkyl group, including substituted and unsubstituted alkyl groups, wherein hetero atoms either may or may not be present in the alkyl group; with the provisos that: (1) when the compound is of the formula

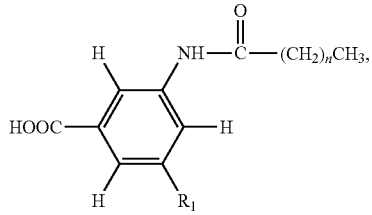

either R$_1$ is not

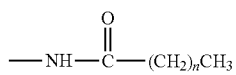

or n is not 9, 10, or 11; (2) when the compound is of the formula

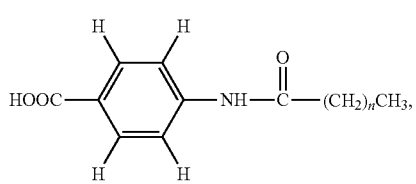

n is not 9, 10, or 11; (3) when the compound is of the formula

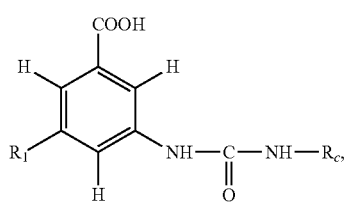

either R$_1$ is not —COOH or R$_c$ is not

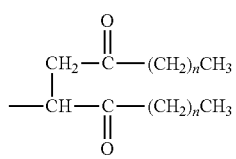

wherein n is 8 to 10; and (4) when the compound is of the formula

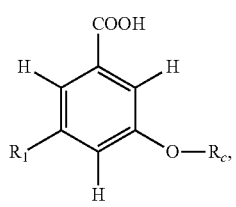

either $R_1$ is not —COOH or $R_c$ is not

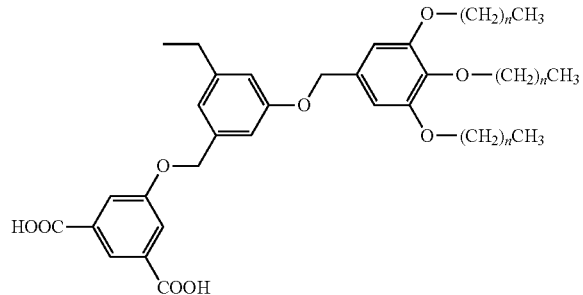

wherein n is from 8 to 10; and (b) an organic liquid; wherein the alkylated aromatic acid compound is present in the organic liquid in an amount of no more than about 5% by weight; and wherein the organogel exhibits a gel-to-sol transition temperature of from about 65° C. to about 110° C. Further disclosed herein is a composition comprising an organogel which comprises: (a) an alkylated aromatic acid compound of the formula

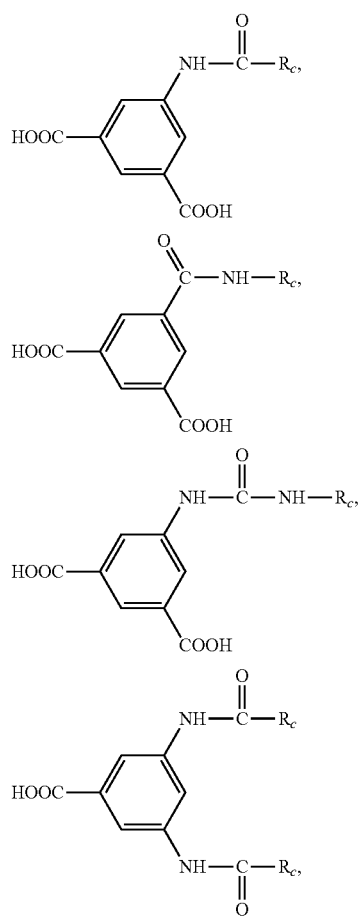

or mixtures thereof, wherein $R_c$ is: (i) a linear unsubstituted alkyl group of the formula —$(CH_2)_nCH_3$, wherein n is an integer; (ii) a branched unsubstituted alkyl group of the formula

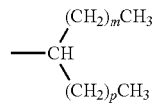

wherein m is an integer and p is an integer; (iii) a branched unsubstituted alkyl group of the formula

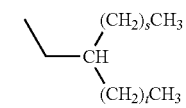

wherein s is an integer and t is an integer; (iv) a branched unsubstituted alkyl group of the formula

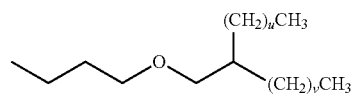

wherein u is an integer and v is an integer; (v) a multi-branched unsubstituted alkyl group of the formula

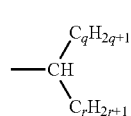

wherein q is an integer and r is an integer; or mixtures thereof; with the proviso that when the compound is of the formula

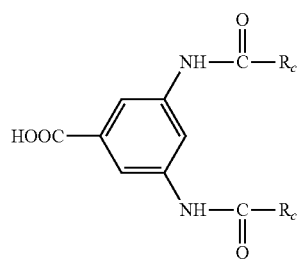

and $R_c$ is a linear unsubstituted alkyl group of the formula —$(CH_2)_nCH_3$, n is not 9, 10, or 11; and (b) an organic liquid.

DETAILED DESCRIPTION

The alkylated aromatic acid compounds disclosed herein form gels by dissolution in an organic liquid with heating, and then cooling the resulting solution to result in gel formation. This process is attributable to the hierarchical self-assembly of the alkylated aromatic acid molecules into a porous nanoscale gel network, which can entrap solvent molecules and rigidify the entire volume of liquid.

Aromatic acids can form reversible hydrogen bonds, resulting in the formation of oligomers or supramolecular polymers held together by non-covalent hydrogen bonds instead of covalent bonds. Some examples of hydrogen-bonding motifs for aromatic acids include the following:

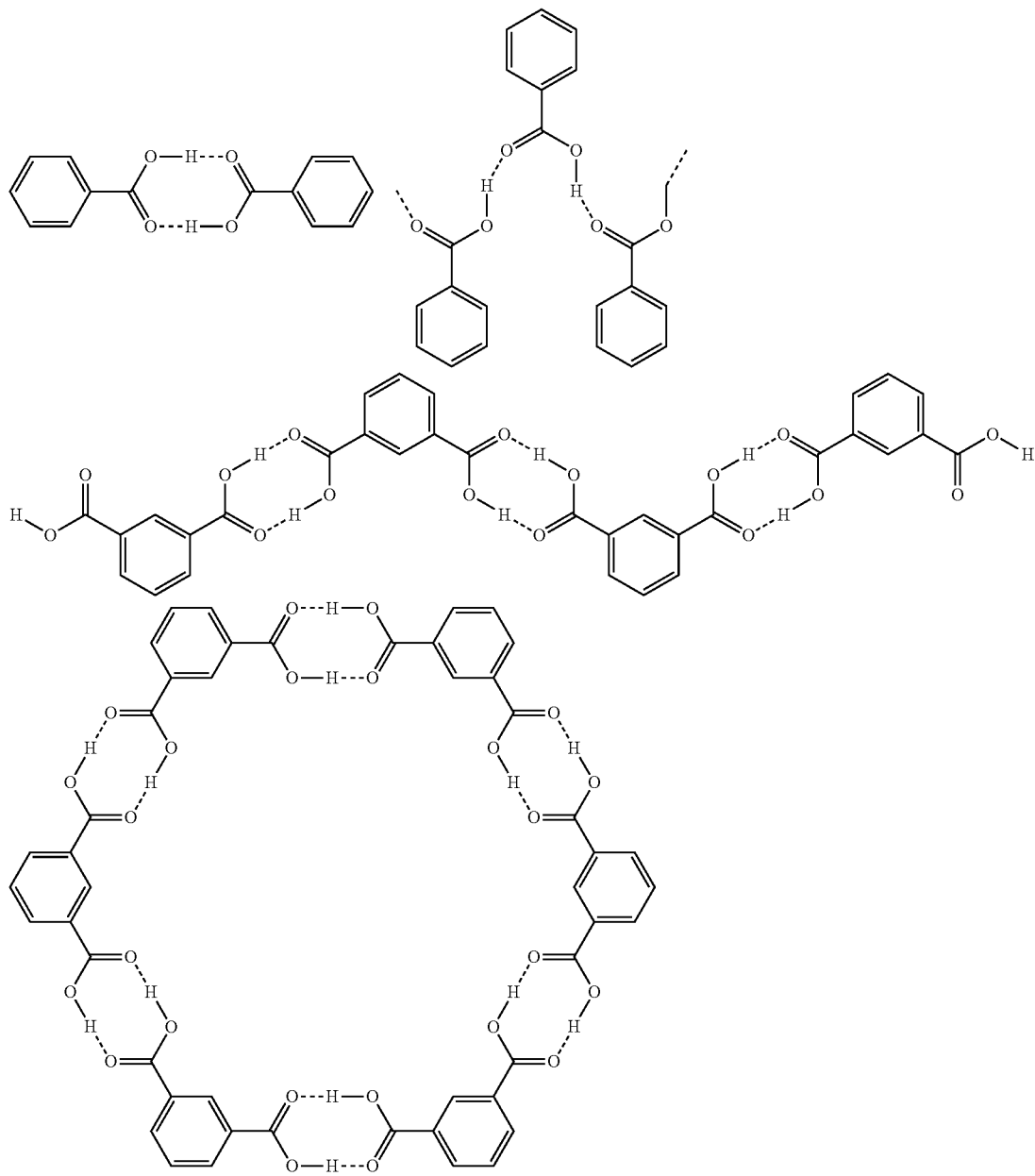

While many aromatic acid compounds form hydrogen-bonded structures and self-assembling nanostructures, most of these structures are hard and highly crystalline in nature.

The organogels disclosed herein are formed with alkylated aromatic acid compounds. These compounds include compounds of the formulae

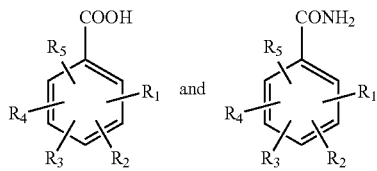

wherein $R_1$, $R_2$, $R_3$, $R_4$, and $R_5$ each, independently of the other, are:

(a) hydrogen atoms;

(b) alkyl groups, including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group, in one embodiment with at least about 1 carbon atom, in another embodiment with at least about 6 carbon atoms, and in yet another embodiment with at least about 12 carbon atoms, and in one embodiment with no more than about 100 carbon atoms, in another embodiment with no more than about 50 carbon atoms, and in yet another embodiment with no more than about 36 carbon atoms, although the number of carbon atoms can be outside of these ranges;

(c) aryl groups, including substituted and unsubstituted aryl groups, wherein hetero atoms, such as oxygen, nitrogen, sulfur, silicon, phosphorus, boron, or the like either may or may not be present in the aryl group, in one embodiment with at least about 5 carbon atoms, in another embodiment with at least about 6 carbon atoms, and in yet another embodiment with at least about 12 carbon atoms, and in one embodiment with no more than about 100 carbon atoms, in another embodiment with no more than about 50 carbon atoms, and in yet another embodiment with no more than about 36 carbon atoms, although the number of carbon atoms can be outside of these ranges, such as phenyl or the like;

(d) arylalkyl groups, including substituted and unsubstituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group, in one embodiment with at least about 6 carbon atoms, in another embodiment with at least about 7 carbon atoms, and in yet another embodiment with at least about 12 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges, such as benzyl or the like; or (e) alkylaryl groups, including substituted and unsubstituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group, in one embodiment with at least about 6 carbon atoms, in another embodiment with at least about 7 carbon atoms, and in yet another embodiment with at least about 12 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges, such as benzyl or the like;

provided that at least one of $R_1$, $R_2$, $R_3$, $R_4$, and $R_5$ is $-X-R_c$, wherein:

(f) $-X-$ is a linking group between $R_c$ and the aromatic group, with examples including (but not being limited to):
(i) $-O-$;
(ii) $-S-$;
(iii) $-SO-$;
(iv) $-SO_2-$;
(v) $-NH-(C=O)-$;
(vi) $-(C=O)-NH-$;
(vii) $-NH-(C=S)-$;
(viii) $-(C=S)-NH-$;
(ix) $-NH-$;
(x) $-NH-(C=O)-NH-$;
(xi) $-NH-(C=S)-NH-$;
(xii) $-NH-(C=O)-O-$;
(xiii) $-NH-(C=O)-S-$;
(xiv) $-O-(C=O)-NH-$;
(xv) $-S-(C=O)-NH-$;
(xvi) $-NH-(C=S)-O-$;
(xvii) $-NH-(C=S)-S-$;
(xviii) $-O-(C=S)-NH-$;
(xix) $-S-(C=S)-NH-$;
(xx) $-(C=O)-O-$;
(xxi) $-(C=O)-S-$;
(xxii) $-O-(C=O)-$;
(xxiii) $-S-(C=O)-$;
(xxiv) $-(C=S)-O-$;
(xxv) $-(C=S)-S-$;
(xxvi) $-O-(C=S)-$;
(xxvii) $-S-(C=S)-$;
(xxviii) $-O-(C=O)-O-$;
(xxix) $-O-(C=S)-O-$;

or the like, as well as combinations thereof;

$R_c$ is an alkyl group, including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group, in one embodiment with at least about 6 carbon atoms, in another embodiment with at least about 12 carbon atoms, and in yet another embodiment with at least about 18 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges;

wherein the substituents on the substituted alkyl, aryl, arylalkyl, and alkylaryl groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring.

In one specific embodiment, exactly one of $R_1$, $R_2$, $R_3$, $R_4$, and $R_5$ is $-X-R_c$. In another specific embodiment, exactly two of $R_1$, $R_2$, $R_3$, $R_4$, and $R_5$ are each, independently of the other, an $-X-R_c$ group. In another specific embodiment, exactly one of $R_1$, $R_2$, $R_3$, $R_4$, and $R_5$ is $-X-R_c$ and exactly one of $R_1$, $R_2$, $R_3$, $R_4$, and $R_5$ is $-COOH$ or $-CONH_2$.

In one specific embodiment, the compound is of the formulae

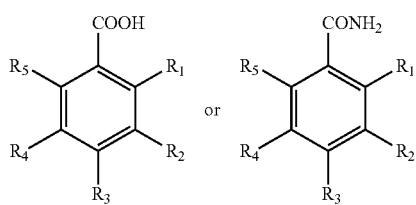

wherein $R_1$, $R_3$, and $R_5$ are each hydrogen atoms. In a further specific embodiment, $R_1$, $R_3$, and $R_5$ are each hydrogen atoms, $R_2$ is $-X_1-R_{c1}$, and $R_4$ is $-COOH$, $-CONH_2$, or $-X_2-R_{c2}$, wherein $X_1$ and $X_2$ can be either the same as or different from each other, and $R_{c1}$ and $R_{c2}$ can be either the same as or different from each other. In a further specific embodiment, the compound is of the formula

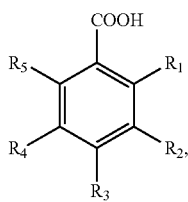

$R_1$, $R_3$, and $R_5$ are each hydrogen atoms, $R_2$ is —$X_1$—$R_{c1}$, and $R_4$ is —COOH or —$X_2$—$R_{c2}$, wherein $X_1$ and $X_2$ can be either the same as or different from each other and $R_{c1}$ and $R_{c2}$ can be either the same as or different from each other.

The above formulas encompass structures of the formula

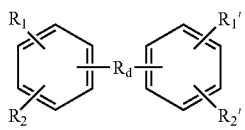

wherein $R_1'$ has the same definition as $R_1$ and can be either the same as or different from $R_1$, $R_2'$ has the same definition as $R_2$ and can be either the same as or different from $R_2$, and $R_d$ is a difunctional moiety that bridges two or more aromatic acid groups, with examples of suitable $R_d$ groups including (but not being limited to):

(a) —$(CH_2)_n$—;
(b) —X—$(CH_2)_n$—X'—;
(c) —$[(XCH_2CH_2)_n]X'$—;
(d) —$[(C=O)—(CH_2)_n—(C=O)]$—;
(e) —X—$[(C=O)—(CH_2)_n—(C=O)]$—X'—;
(f) —X—$[(C=O)—X'—(CH_2)_n—X''—(C=O)]$—X'''—;
(g) —$[(C=O)—X—(CH_2)_n—X'—(C=O)]$—;

or the like, wherein X, X', X", and X''' each, independently of the other, are defined as O, S, or NH, and n is an integer, in one embodiment at least about 1, and in one embodiment no more than about 50. Specific examples of $R_d$ also include large branched alkylated functional groups such as

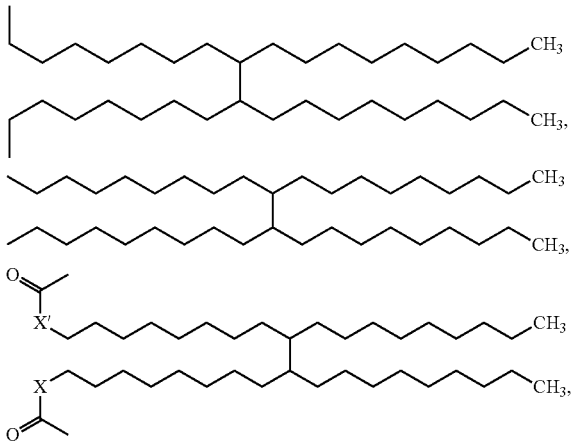

or the like, as well as mixtures thereof, wherein X, X', X", and X''' each, independently of the other, are defined as O, S, or NH.

Specific examples of $R_c$ groups include (but are not limited to):

(a) linear unsubstituted alkyl groups of the formula —$(CH_2)_n CH_3$, wherein n is in one embodiment at least about 5, in another embodiment at least about 11, and in yet another embodiment at least about 15, and in one embodiment no more than about 50, in another embodiment no more than about 35, and in yet another embodiment no more than about 25, although the value of n can be outside of these ranges, including specific values such as:

(i) 17;
(ii) 15;
(iii) 11;

or the like; and (b) branched unsubstituted alkyl groups of the formula

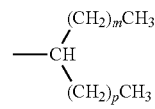

wherein m is in one embodiment 0, in another embodiment at least 1, and in yet another embodiment at least about 3, and in one embodiment no more than about 17, in another embodiment no more than about 11, and in yet another embodiment no more than about 5, although the value of m can be outside of these ranges, and wherein p is in one embodiment 0, in another embodiment at least 1, and in yet another embodiment at least about 3, and in one embodiment no more than about 17, in another embodiment no more than about 11, and in yet another embodiment no more than about 5, although the value of p can be outside of these ranges, including specific values such as:

(i) m=11, p=9;
(ii) m=5, p=3;
(iii) m=7, p=5;

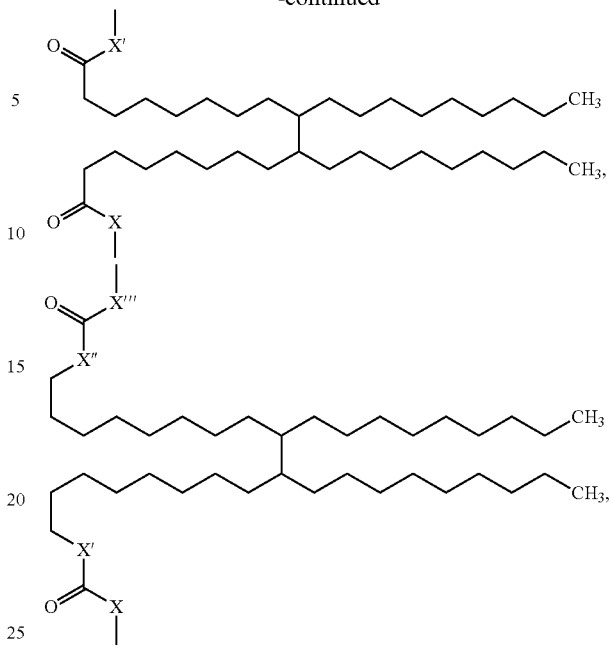

(c) branched unsubstituted alkyl groups of the formula

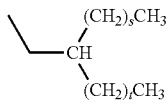

wherein s is an integer, in one embodiment 0, in another embodiment at least about 1, and in yet another embodiment at least about 3, and in one embodiment no more than about 49, in another embodiment no more than about 17, and in yet another embodiment no more than about 5, although the value of s can be outside of these ranges, and wherein t is an integer, in one embodiment 0, in another embodiment at least about 1, and in yet another embodiment at least about 3, and in one embodiment no more than about 49, in another embodiment no more than about 17, and in yet another embodiment no more than about 5, although the value of t can be outside of these ranges;

(d) branched unsubstituted alkyl groups of the formula

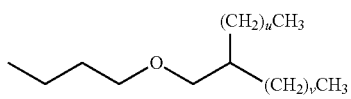

wherein u is an integer, in one embodiment 0, in another embodiment at least about 1, and in yet another embodiment at least about 3, and in one embodiment no more than about 49, in another embodiment no more than about 17, and in yet another embodiment no more than about 5, although the value of u can be outside of these ranges, and wherein v is an integer, in one embodiment 0, in another embodiment at least about 1, and in yet another embodiment at least about 3, and in one embodiment no more than about 49, in another embodiment no more than about 17, and in yet another embodiment no more than about 5, although the value of v can be outside of these ranges;

(e) multi-branched unsubstituted alkyl groups of the formula

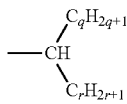

wherein q is an integer, in one embodiment at least about 1, in another embodiment at least about 4, and in yet another embodiment at least about 6, and in one embodiment no more than about 18, in another embodiment no more than about 12, and in yet another embodiment no more than about 10, although the value of q can be outside of these ranges, and wherein r is an integer, in one embodiment at least about 1, in another embodiment at least about 4, and in yet another embodiment at least about 6, and in one embodiment no more than about 18, in another embodiment no more than about 12, and in yet another embodiment no more than about 10, although the value of r can be outside of these ranges, including specific values such as:

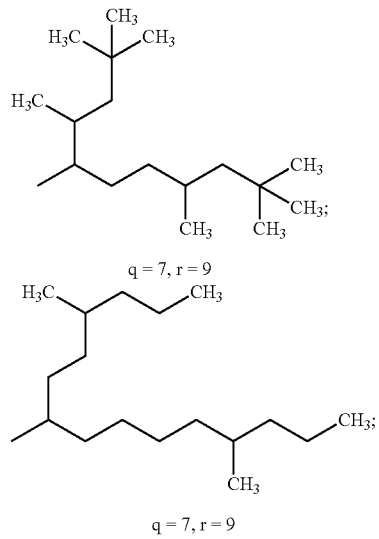

or the like, as well as mixtures thereof.

In a specific embodiment, $R_1$, $R_2$, $R_3$, $R_4$, and/or $R_5$ on an aromatic carbon atom adjacent to —$CONH_2$ can be joined with —$CONH_2$ to form a ring, as in, for example, the compounds with the following structure:

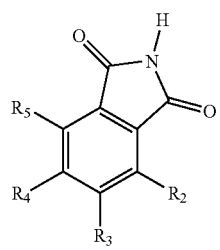

and in a more specific embodiment,

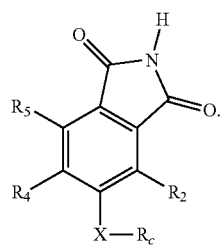

Some specific examples of suitable compounds include those of the formula

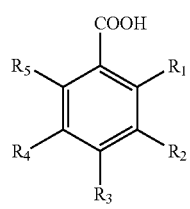

wherein $R_1$, $R_3$, and $R_5$ are each hydrogen atoms and:
(a) $R_2$ is —COOH and $R_4$ is

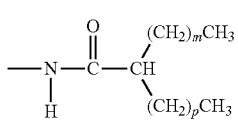

wherein m is 11 and p is 9;
(b) $R_2$ is —COOH and $R_4$ is

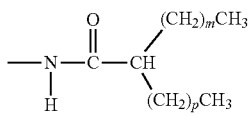

wherein m is 5 and p is 3;
(c) $R_2$ is —COOH and $R_4$ is

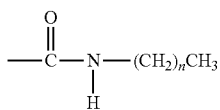

wherein n is 17;
(d) $R_2$ is —COOH and $R_4$ is

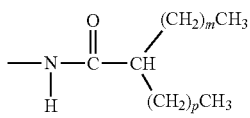

wherein m is 7 and p is 5;
(e) $R_2$ is —COOH and $R_4$ is

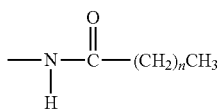

wherein n is 15;
(f) $R_2$ is —COOH and $R_4$ is

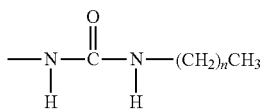

wherein n is 11;
(g) $R_2$ is —COOH and $R_4$ is

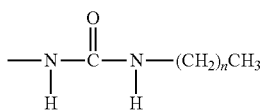

wherein n is 17;

(h) $R_2$ is

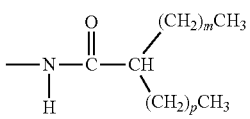

wherein m is 11 and p is 9, and $R_4$ is

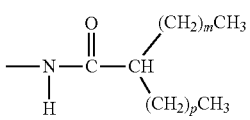

wherein m is 11 and p is 9;
(i) $R_2$ is

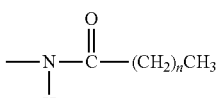

wherein n is 17 and $R_4$ is

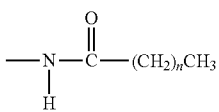

wherein n is 17; or the like.

Alkylated aromatic acid compounds can be prepared as disclosed in, for example, U.S. Pat. No. 7,905,954 and Copending Application U.S. Ser. No. 12/820,497, the disclosures of each of which are totally incorporated herein by reference.

The aromatic acid compounds disclosed herein can be used to form organogels with an organic liquid. Any desired or effective organic liquid can be used, including (but not limited to) hydrocarbons, including aliphatic and aromatic hydrocarbons, alcohols, amines, esters, ethers, mercaptans, acids (including carboxylic acids, sulfonic acids, or the like, as well as mixtures thereof), sulfones, anhydrides, siloxanes, polymeric liquids, or the like, as well as mixtures thereof.

Specific examples of suitable organic liquids include (but are not limited to):

linear, branched, and/or cyclic unsubstituted aliphatic hydrocarbons, such as butanes, pentanes, such as n-pentane, isopentane, neopentane, cyclopentane, or the like, hexanes, such as n-hexane, isohexane, neohexane, cyclohexane, or the like, heptanes, such as n-heptane, isoheptane, neoheptane, cycloheptane, or the like, octanes, such as n-octane, isooctane, neooctane, cyclooctane, or the like, nonanes, decanes, such as n-decane, isodecane, neodecane, decadehydronaphthalene, or the like, undecanes, dodecanes, such as n-dodecane, isododecane, neododecane, or the like, as well as mixtures thereof;

linear, branched, and/or cyclic substituted aliphatic hydrocarbons, such as chloromethane, bromomethane, iodomethane, dichloromethane, dibromomethane, bromochloromethane, dichlorofluoromethane, trichlorofluoromethane, chlorodifluoromethane, chloroform, bromoform carbon tetrachloride, dichloroethanes, dibromoethanes, trichloroethanes, ethyl iodide, propyl iodides, butyl iodides, tetrachloroethanes, tetrachloroethylene, or the like, as well as mixtures thereof;

unsubstituted aromatic and heteroaromatic hydrocarbons, such as benzene, toluene, xylenes, mesitylene, styrene, pyridine, pyrrole, furan, pyrazine, or the like, as well as mixtures thereof;

substituted aromatic and heteroaromatic hydrocarbons, such as fluorobenzene, chlorobenzene, bromobenzene, iodobenzene, nitrobenzene, or the like, as well as mixtures thereof;

linear, branched, and/or cyclic unsubstituted aliphatic alcohols, such as methanol, ethanol, propanols, butanols, pentanols, hexanols, heptanols, octanols, nonanols, decanols, undecanols, dodecanols, or the like, as well as mixtures thereof;

aliphatic and aromatic amines, such as methyl amine, ethyl amine, propyl amine, butylamine, pentylamine, hexylamine, octylamine, decylamine, dodecylamine, triethyl amine, diisopropyl ethyl amine, aniline, methyl anthranilate, or the like, as well as mixtures thereof;

fatty acids, such as caprylic acid, lauric acid, myristic acid, palmitic acid, stearic acid, unsaturated fatty acids such as oleic acid and linoleic acid, fatty acid oils such as soybean oil, canola oil, olive oil, tung oil, sunflower oil, safflower oil, hemp oil, cottonseed oil, palm oil, corn oil, or the like, as well as mixtures thereof;

aliphatic and aromatic esters, such as methyl acetate, ethyl acetate, butyl acetate, amyl acetate, methyl hexanoate, methyl octanoate, methyl myristate, methyl oleate, methyl linoleate, methyl benzoate, ethyl benzoate, benzyl benzoate, or the like, as well as mixtures thereof;

aliphatic and aromatic ethers, such as diethyl ether, dipropyl ethers, dibutyl ethers, dipentyl ethers, anisole, diphenyl ether, or the like, as well as mixtures thereof;

with examples of suitable substituents including (but not being limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring;

or the like, as well as mixtures thereof.

The alkylated aromatic acid compound is present in the organic liquid in any desired or effective amount to form an organogel, in one embodiment at least about 0.05% by weight, in another embodiment at least about 0.1% by weight, and in yet another embodiment at least about 1% by weight, and in one embodiment no more than about 20% by weight, in another embodiment no more than about 10% by weight, in yet another embodiment no more than about 5% by weight, and in still another embodiment no more than about 1% by weight, although the amount can be outside of these ranges.

The organogel compositions disclosed herein in one embodiment comprise an organogelator comprising an alkylated aromatic acid compound and an organic liquid. In one specific embodiment, the organogelator component of the organogel consists essentially of an alkylated aromatic acid compound or mixture of alkylated aromatic acid compounds. In another specific embodiment, the organogelator component of the organogel consists of an alkylated aromatic acid compound or mixture of alkylated aromatic acid compounds. These embodiments are in contrast to other embodiments wherein the organogelator comprises an alkylated aromatic acid compound and another moiety which, in combination, gel the organic liquid. In embodiments wherein the organogelator component consists essentially of an alkylated aromatic acid compound or mixture of alkylated aromatic acid compounds, or wherein the organogelator component consists of an alkylated aromatic acid compound or mixture of alkylated aromatic acid compounds, other components can be present in the organogels, but none of these other components have the action or function of combining with the alkylated aromatic acid compound or mixture thereof to gel the organic liquid.

The organogels disclosed herein exhibit gel-to-sol transition temperatures of in one embodiment at least about 65° C., in another embodiment at least about 80° C., and in yet another embodiment at least about 95° C., and in one embodiment no more than about 110° C., and in another embodiment no more than about 105° C., although the temperature can be outside of these ranges.

The organogel compositions disclosed herein can be used in a wide variety of applications, including (but not limited to) thickening agents for numerous products, such as paints, coatings, lubricants, adhesives, personal care products, pharmaceutical and dermatological gels, and even in certain food products, and they can be used in tissue engineering, biomineralization (as templates), catalysis, gel-based scaffolds for energy transfer and light harvesting, and the like.

Specific embodiments will now be described in detail. These examples are intended to be illustrative, and the claims are not limited to the materials, conditions, or process parameters set forth in these embodiments. All parts and percentages are by weight unless otherwise indicated.

The compounds in the Examples were used to gel organic liquids by the vial inversion method as described in, for example, Fages, F. *Low Molecular Mass Gelators*, Vol. 256, 2005 in *Topics in Current Chemistry*, the disclosure of which is totally incorporated herein by reference. Gels were prepared by placing a specified amount of gelator powder in a vial with an appropriate organic solvent. The mixtures were then heated to a specified temperature for a certain period of time until a homogeneous mixture or clear solution was obtained, followed by cooling and standing at room temperature for at least 30 min. The gels were then qualitatively evaluated using the "inversion test," which entailed inverting the gel sample and observing the flow behavior. If the material did not flow or fall under its own weight under gravity, the material was classified as a gel.

The "dropping ball" method was used to determine the gel-to-sol transition temperature. A stainless steel ball (2 mm diameter) was carefully placed on the top of the gel formed. The vessel, a 1 dram vial with an outer diameter of 15 mm and a height of 45 mm, containing the gel was sealed and slowly heated in an oil bath at a rate of approximately 1-2° C./min. The temperature at which the ball touched the bottom of the vial was taken to be the gel-to-sol transition temperature.

Example I

Synthesis of 5-(2'-decyltetradecanamido)isophthalic acid

Step 1: Synthesis of 2-decyltetradecanoyl chloride

2-Decyltetradecanoic acid (ISOCARB 24, obtained from Sasol America, Tex., 7.65 g, 20.8 mmol) and a catalytic amount of N,N'-dimethylformamide (0.28 mL, 3.62 mmol) were dissolved in dry tetrahydrofuran (100 mL) under an inert atmosphere. The mixture was cooled to 0° C. and oxalyl chloride (7.3 mL, 83.7 mmol, obtained from Sigma-Aldrich, Milwaukee, Wis.) was added dropwise slowly and allowed to stir for at least 10 min until the evolution of hydrochloric acid gas had ceased. The mixture was allowed to warm slowly to room temperature over 3 h before the solvent was removed by rotary evaporation to afford the acid chloride compound as a viscous, pale yellow syrup, which was used in the next step without further purification.

Step 2: Synthesis of 5-(2'-decyltetradecanamido)isophthalic acid

A suspension of 2-decyltetradecanoyl chloride from Step 1 in dry tetrahydrofuran (80 mL) was added dropwise slowly to a suspension of dimethyl 5-aminoisophthalate (Sigma-Aldrich, 4.40 g, 21.0 mmol), triethyl amine (4.4 mL, 31.5 mmol), and dry tetrahydrofuran (100 mL) under an inert atmosphere at 0° C. The reaction was allowed to warm slowly to room temperature and was stirred overnight. Deionized water (10 mL) was added and the tetrahydrofuran was removed by rotary evaporation. The crude residue was then dissolved in 250 mL of ethyl acetate and washed with 3 successive 100 mL portions of deionized water. The ethyl acetate was then removed from the organic phase by rotary evaporation and the product was dried in vacuo to give crude dimethyl 5-(2'-decyltetradecanamido)isophthalate (12.56 g) as a pale yellow solid.

Step 3: Saponification of Dimethyl 5-(2'-decyltetradecanamido)isophthalate

Dimethyl 5-(2'-decyltetradecanamido)isophthalate (12.56 g) from Step 2, potassium hydroxide (4.67 g, 0.0832 mol), and methanol (100 mL) were added to a 500 mL vessel and the mixture was heated and maintained at reflux overnight. The reaction was then cooled to room temperature to give a turbid red-orange mixture. The mixture was subsequently acidified with hydrochloric acid (7 mL) to give a white precipitate, which was collected by suction filtration, washed with deionized water, and then dried in vacuo to give an off-white powder (11.7 g). The product was identified by $^1$H and $^{13}$C NMR spectroscopy and ESI-MS and was of satisfactory purity. The product was believed to be of the formula

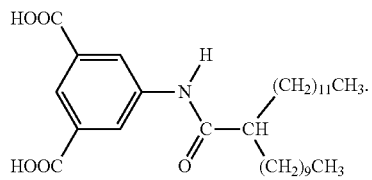

Gelation of Toluene and Organogel Formation 5-(2'-Decyltetradecanamido)isophthalic acid was used for gelling toluene. The compound as prepared in the steps above (11.9 mg) and toluene (1 mL) were placed in a sealed vessel and mixed and heated until a clear, homogeneous solution was obtained. After slowly cooling and allowing the vessel to stand at room temperature for at least 30 min, a transparent gel was formed, which did not fall or flow upon inverting the vessel.

Inversion tests were also repeated at varied concentrations of 5-(2'-decyltetradecanamido)isophthalic acid in toluene, and the MGC was determined to be 0.7 wt %.

Additional organogels were formed with 5-(2'-decyltetradecanamido)isophthalic acid in other organic solvents. Gel-to sol temperatures ($T_{GS}$) values were measured for some of these organogels at a gelator concentration of 10 wt. %. The results were as follows:

| Solvent | Appearance | MGC (wt. %) | $T_{GS}$ (° C.) |
| --- | --- | --- | --- |
| ethanol | opaque gel | <10.0 | — |
| 1-hexanol | opaque gel | <10.0 | — |
| ethyl acetate | opaque gel | <10.0 | — |
| chloroform | transparent gel | 1.0 | 68 |
| tetrahydrofuran | opaque gel | <10.0 | — |
| cyclohexane | transparent gel | 1.0 | 89.5 |
| decalin | transparent gel | 0.5 | — |
| benzene | transparent gel | 2.0 | — |
| toluene | transparent gel | 0.7 | 68 |
| xylenes | transparent gel | 0.7 | — |
| mesitylene | transparent gel | <0.4 | — |
| chlorobenzene | transparent gel | 0.3 | — |
| styrene | transparent gel | <8.0 | — |
| dodecane | transparent gel | <4.0 | — |
| hexadecane | transparent gel | 0.6 | 102 |
| paraffin oil | transparent gel | 2.0 | — |
| 1,2-dimethoxyethane | opaque gel | 0.3 | 80 |

— = not determined

Example II

Synthesis of 5-hexadecanamidoisophthalic acid

Dimethyl 5-aminoisophthalate (Aldrich, 3.28 g, 15.7 mmol) and triethyl amine (3.4 mL, 24.7 mmol) were dissolved in dry tetrahydrofuran (90 mL) under inert atmosphere and cooled to 0° C. for at least 30 min. A solution of palmitoyl chloride (5 mL, 16.5 mmol) in THF (25 mL) was then added slowly, dropwise. The reaction was then allowed to warm slowly to room temperature and stirred for at least 1 h before deionized water (10 mL) was added and the tetrahydrofuran was removed by rotary evaporation. The crude residue was then suspended in deionized water (50 mL), filtered, washed with deionized water, and dried to give a white solid. The crude solid was then dissolved in refluxing methanol (200 mL). Potassium hydroxide (~85%, 5.76 g, 0.102 mol) and deionized water (50 mL) were then added. After 1 h, the reaction was cooled to room temperature to give a cloudy white suspension. 5M HCl (25 mL) was added until the pH of the slurry was acidic, and the solid was filtered, washed with deionized water, and dried in vacuo to give a white solid (6.45 g, 98%). The product was identified by $^1$H and $^{13}$C NMR spectroscopy and ESI-MS and was of satisfactory purity. The product was believed to be of the formula

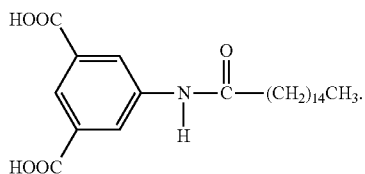

Gelation of Decalin and Organogel Formation

5-Hexadecanamidoisophthalic acid was used for decalin. The compound as prepared in the steps above (8.2 mg) and decalin (1 mL) were placed in a sealed vessel and mixed and heated until a clear, homogeneous solution was obtained. After slowly cooling and allowing the vessel to stand at room temperature for at least 30 min, a transparent gel was formed, which did not fall or flow upon inverting the vessel.

Inversion tests were also repeated at varied concentrations of 5-hexadecanamidoisophthalic acid in decalin, and the MGC was determined to be 0.8 wt %.

Additional organogels were formed with 5-hexadecanamidoisophthalic acid in other organic solvents. The results were as follows:

| Solvent | Appearance | MGC (wt. %) |
|---|---|---|
| ethylene glycol | opaque gel | 0.5 |
| decalin | transparent gel | 0.8 |
| hexadecane | transparent gel | 0.3 |

Example III

Synthesis of 5-(2'-butyloctanamido)isophthalic acid]

Step 1: Synthesis of 2-butyloctanoyl chloride

2-Hexyldecanoic acid (ISOCARB 12, obtained from Sasol America, Tex., 11.43 g, 57.1 mmol) and dry tetrahydrofuran (200 mL) were added to a 500 mL single-neck round-bottom flask under an inert atmosphere. A catalytic amount of N,N'-dimethylformamide (0.3 mL, 3.87 mmol) was then added, followed by the slow, dropwise addition of oxalyl chloride (7.0 mL, 80.2 mmol). The mixture was stirred for 10 min until evolution of hydrochloric acid gas had ceased, before slowly warming to room temperature over 2 h. Rotary evaporation of the THF afforded the acid chloride 2-butyloctanoyl chloride as a brown oil, which was dried in vacuo prior to use in Step 2.

Step 2: Synthesis of dimethyl 5-(2'-butyloctanamido)isophthalic acid

A solution of 2-butyloctanoyl chloride from Step 1 in dry tetrahydrofuran (50 mL) was slowly added dropwise to another solution of dimethyl 5-aminoisophthalate (Aldrich Chemical Co., 11.08 g, 53.0 mmol) and triethyl amine (11.0 mL, 78.9 mmol) in tetrahydrofuran (250 mL) under an inert atmosphere at 0° C. The mixture was then allowed to warm slowly to room temperature and was stirred overnight. Deionized water (10 mL) was added and the tetrahydrofuran was removed by rotary evaporation. The crude residue was then dissolved in 200 mL of diethyl ether, and was washed successively with saturated sodium bicarbonate (60 mL), deionized water (60 mL), and brine (60 mL). The organic phase was then dried over sodium sulfate and filtered before removing the diethyl ether by rotary evaporation. Crude dimethyl 5-(2-butyloctanamido)isophthalic acid (21.71 g) was obtained as an amber oil after drying in vacuo.

Step 3: Saponification of dimethyl 5-(2'-butyloctanamido)isophthalate

Dimethyl 5-(2'-butyloctanamido)isophthalate from Step 2, potassium hydroxide (85%, 29.61 g, 0.0527 mol), and methanol (200 mL) were heated and maintained at reflux overnight. The reaction was then cooled to room temperature to give a turbid red-orange mixture. The mixture was then acidified with hydrochloric acid to give a white precipitate, which was collected by suction filtration, washed with deionized water, and then dried in vacuo to give a white powder (18.94 g). The product was identified by $^1$H and $^{13}$C NMR spectroscopy and ESI-MS and was of satisfactory purity. The product was believed to be of the formula

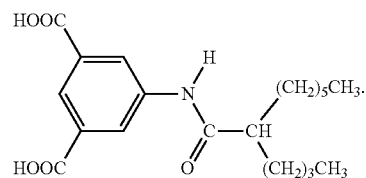

Gelation of Xylenes using 5-(2'-butyloctanamido)isophthalic acid

A 0.56 Molar ethanolic solution of 5-(2'-butyloctanamido) isophthalic acid from the above steps (50 µL, 28.0 µmol), 10.1 mg) was added to xylenes (1 mL) and gently agitated for a few seconds. Upon standing, the mixture solidified into a turbid gel, which did not fall or flow upon inverting the vessel.

Example IV

Synthesis of 3,5-bis(2'-decyltetradecanamido)benzoic acid

Step 1: Synthesis of 2-decyltetradecanoyl chloride

2-Decyltetradecanoic acid (ISOCARB 24, obtained from Sasol America, 1.15 g, 3.13 mmol) and dry tetrahydrofuran (20 mL) were mixed in a 100 mL vessel with stirring under inert atmosphere. The mixture was cooled to 0° C. for at least 30 min, after which a catalytic amount of N,N'-dimethylformamide (4 drops) was added, followed by the slow, dropwise addition of oxalyl chloride (1 mL, 12.6 mmol). The reaction was then allowed to warm slowly to room temperature and allowed to stir for 30 min prior to removing the solvent by rotary evaporation. The acid chloride compound thus obtained was used in the next step without further purification.

Step 2: Synthesis of methyl 3,5-bis(2'-decyltetradecanamido)benzoate 3,5-Diaminobenzoic acid (Sigma-Aldrich) was esterified using a known procedure (Electrochimica Acta 2001, 46, 3955-3962) with thionyl chloride and anhydrous methanol to give the corresponding methyl ester, methyl 3,5-diaminobenzoate. Methyl 3,5-diaminobenzoate (260.8 mg, 1.9 mmol) was dissolved in dry tetrahydrofuran (5 mL) in a 100 mL vessel under inert atmosphere. Triethylamine (0.7 mL, 4.99 mmol) was then added and the solution was cooled to 0° C. A solution of 2-decyltetradecanoyl chloride from Step 1 in dry tetrahydrofuran (10 mL) was then added slowly, dropwise. The reaction was then allowed to warm slowly to room temperature. After stirring overnight, the reaction was quenched with water and the tetrahydrofuran was removed by rotary evaporation. The crude product residue was then dissolved in diethyl ether (50 mL) and washed with deionized water (20 mL). The ether layer was separated and concentrated to give methyl 3,5-bis(2'-decyltetradecanamido)benzoate as a pale pink solid (1.17 g).

Step 3: Saponification of methyl 3,5-bis(2'-decyltetradecanamido)benzoate

Methyl 3,5-bis(2'-decyltetradecanamido)benzoate from Step 2, potassium hydroxide (0.38 g, 5.77 mmol), and methanol (20 mL) were added to a 50 mL vessel and heated to reflux. Deionized water (10 mL) was then added and the reaction was held at reflux overnight. The reaction was then cooled to room temperature, which resulted in the formation of an oil phase. Diethyl ether (20 mL) was added and the aqueous phase was removed. The organic phase was then washed successively with 1 Molar hydrochloric acid (30 mL), 0.1 Molar hydrochloric acid (30 mL), and deionized water twice (30 mL each), before concentrating the ether layer by rotary evaporation and drying in vacuo to give 3,5-bis(2'-decyltetradecanamido)benzoic acid as a light brown waxy solid (1.33 g, 99%). The product was identified by $^1$H and $^{13}$C NMR spectroscopy and ESI-MS and was of satisfactory purity. The product was believed to be of the formula

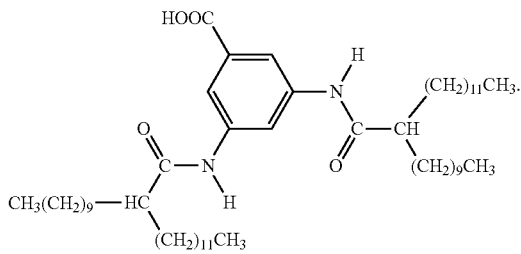

Gelation of Paraffin Oil and Organogel Formation 3,5-bis(2'-decyltetradecanamido)benzoic acid was used for gelling paraffin oil. The compound as prepared in the steps above (43.8 mg) and paraffin oil (1 mL) were placed in a sealed vessel and mixed and heated until a clear, homogeneous solution was obtained. After slowly cooling and allowing the vessel to stand at room temperature for at least 30 min, a transparent gel was formed, which did not fall or flow upon inverting the vessel.

Additional organogels were formed with 3,5-bis(2'-decyltetradecanamido)benzoic acid in other organic solvents. The results were as follows:

| Solvent | Appearance | Concentration (wt. %) |
|---|---|---|
| cyclohexane | transparent gel | 10.1 |
| hexanes | transparent gel | 5.0 |
| paraffin oil | transparent gel | 4.4 |

Example V

Synthesis of 5-(octadecylureido)isophthalate

Step 1: Synthesis of dimethyl 5-(octadecylureido)isophthalate

Dimethyl 5-aminoisophthalate (obtained from Aldrich Chemical Co., Milwaukee, Wis., 0.441 g, 2.12 mmol) was dissolved in dry N,N-dimethylformamide (8 mL) in a 50 mL round-bottom flask under inert atmosphere. A 2.12 Molar solution of octadecylisocyanate (2.12 mmol) in dry N,N-dimethylformamide (1 mL) was then added dropwise. The residual octadecylisocyanate solution was quantitatively transferred with 2 portions of N,N-dimethylformamide (1 mL each) and the reaction was stirred overnight at room temperature. The reaction was then heated to 100° C. for 22 h, and thereafter cooled to room temperature to give a white slurry. The solid was then vacuum filtered, washed with fresh N,N-dimethylformamide, and then washed with deionized water. The filtrate was concentrated by rotary evaporation to give a white solid.

Step 2: Saponification of dimethyl 5-(octadecylureido)isophthalate

Crude dimethyl 5-(octadecylureido)isophthalate from Step 1 (330 mg, 0.654 mmol) was suspended in methanol (15 mL). Potassium hydroxide (0.1983 mg, 3.53 mmol) was then added and the mixture was heated to reflux for 2 h. After cooling to room temperature, the suspended white solid was recovered by filtration and washed with cold methanol. The crude solid was then suspended in 1 Molar hydrochloric acid and stirred for 2 days, after which the product was collected by filtration, washed with deionized water, and dried in vacuo to yield a white powder (124.8 mg). The product was identified by $^1$H and $^{13}$C NMR spectroscopy and ESI-MS and was of satisfactory purity. The product was believed to be of the formula

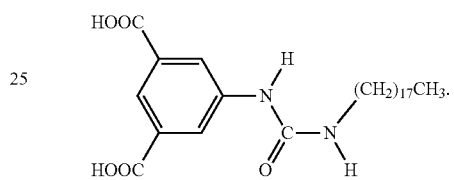

Gelation of Decalin and Organogel Formation 5-(octadecylureido)isophthalate was used for gelling decalin. The compound as prepared in the steps above (43.8 mg) and decalin (1 mL) were placed in a sealed vessel and mixed and heated until a clear, homogeneous solution was obtained. After slowly cooling and allowing the vessel to stand at room temperature for at least 30 min, a turbid gel was formed, which did not fall or flow upon inverting the vessel.

Additional organogels were formed with 5-(octadecylureido)-isophthalate in other organic solvents. The results were as follows:

| Solvent | Appearance | Concentration (wt. %) |
|---|---|---|
| methanol | opaque gel | 1.9 |
| decalin | turbid gel | 2.3 |
| xylenes | transparent gel | 2.0 |

Example VI

Synthesis of 9,10-dinonyloctadecanamidodiisophthalic acid

Step 1: Synthesis of 9,10-dinonyloctadecanedioic acid tetrachloride

PRIPOL® 1006 (96%, 3.23 g, 5.70 mmol, obtained from Uniqema, Del.) and dry tetrahydrofuran (50 mL) were added to a 250 mL round-bottom flask under inert atmosphere. The solution was then cooled to 0° C. for at least 30 min before a catalytic amount of N,N'-dimethylformamide (0.10 mL, 1.3 mmol) was added, followed by the slow, dropwise addition of oxalyl chloride (2.0 mL, 23.3 mmol). The mixture was then slowly allowed to warm to room temperature and stirred for 3.5 h before the solvent was removed by rotary evaporation to afford a colorless liquid with suspended white solid. The 9,10-dinonyloctadecanedioic acid tetrachloride thus obtained was used in the next step without further purification.

Step 2: Synthesis of tetramethyl 9,10-dinonyloctadecanamidodiisophthalic acid 9,10-Dinonyloctadecanedioic acid tetrachloride from Step 1 and dry tetrahydrofuran (50 mL) were mixed under inert atmosphere and the mixture was cooled to 0° C. for at least 30 min. Dimethyl 5-aminoisophthalate (Aldrich, 2.65 g, 12.7 mmol) was then added as a solution in dry N,N'-dimethylformamide (15 mL) slowly, dropwise to the flask containing the tetraacid chloride. Two successive rinses with tetrahydrofuran (10 mL) were done to quantitatively transfer all of the amine to the acid chloride flask. Triethylamine (2.6 mL, 18.7 mmol) was then added and the reaction was thereafter allowed to warm slowly to room temperature and stir overnight. After removing the tetrahydrofuran by rotary evaporation, the crude residue was dissolved in 140 mL diethyl ether and washed with deionized water (40 mL), saturated sodium bicarbonate (40 mL), 5% citric acid (40 mL), and brine (40 mL). The diethyl ether layer was then dried over sodium sulfate and filtered through glass wool, after which the solvent was removed by rotary evaporation and the product was dried in vacuo to give crude tetramethyl 9,10-dinonyloctadecanamidodiisophthalate (5.61 g) as a viscous, yellow syrup. The diester thus obtained was used in the next step without further purification.

Step 3: Saponification of tetramethyl 9,10-dinonyloctadecanamido-diisophthalate

Tetramethyl 9,10-dinonyloctadecanamido-diisophthalate from Step 2, potassium hydroxide (15.38 g, 233 mmol), methanol (200 mL), and deionized water (100 mL) were added to a 500 mL vessel and the mixture was heated to reflux for 1 h. The reaction was then cooled to room temperature and acidified with 5M hydrochloric acid (50 mL) to give a white precipitate, which was collected by suction filtration, washed with deionized water, and then dried in vacuo to give a pale orange-yellow powder (4.62 g, 91%). The product was identified by $^1$H and $^{13}$C NMR spectroscopy and ESI-MS and was of satisfactory purity. The product, tetramethyl 9,10-dinonyloctadecanamidodiisophthalic acid, was believed to be of the formula

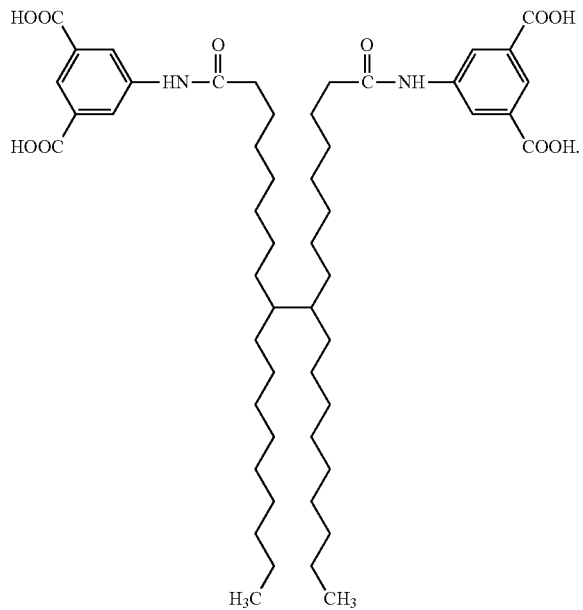 [SMILES: CCCCCCCCCC(CCCCCCCC(=O)Nc1cc(C(=O)O)cc(C(=O)O)c1)C(CCCCCCCCC)CCCCCCCC(=O)Nc1cc(C(=O)O)cc(C(=O)O)c1]

Gelation of Ethylene Glycol and Organogel Formation

Tetramethyl 9,10-dinonyloctadecanamidodiisophthalic acid was used for gelling ethylene glycol. The compound as prepared in the steps above (20.2 mg) and ethylene glycol (1 mL) were placed in a sealed vessel and mixed and heated until a clear, homogeneous solution was obtained. After slowly cooling and allowing the vessel to stand at room temperature for at least 30 min, an opaque gel was formed, which did not fall or flow upon inverting the vessel.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A composition comprising an organogel consisting of a) an alkylated aromatic acid and b) an organic liquid solvent entrapped within the organogel wherein the liquid is rigidified:

wherein the alkylated aromatic acid compound is of the formula

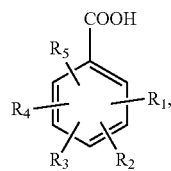

or mixtures thereof, wherein $R_1$, $R_2$, $R_3$, $R_4$, and $R_5$ each, independently of the other, is:

(A) hydrogen atoms; —COOH;

(B) alkyl groups, including substituted and unsubstituted alkyl groups, wherein hetero atoms either may or may not be present in the alkyl group;

(C) aryl groups, including substituted and unsubstituted aryl groups, wherein hetero atoms either may or may not be present in the aryl group;

(D) arylalkyl groups, including substituted and unsubstituted arylalkyl groups, wherein hetero atoms either may or may not be present in either or both of the alkyl portion and the aryl portion of the arylalkyl group; or (E) alkylaryl groups, including substituted and unsubstituted alkylaryl groups, wherein hetero atoms either may or may not be present in either or both of the alkyl portion and the aryl portion of the alkylaryl group;

provided that at least one of $R_1$, $R_2$, $R_3$, $R_4$, and $R_5$ is —X—$R_c$, wherein:

(F) —X— is a linking group between $R_c$ and the aromatic group, wherein —X— is selected from the group consisting of (i) —O—;

(ii) —S—;

(iii) —SO—;

(iv) —SO$_2$—;

(v) —NH—(C═O)—;

(vi) —(C═O)—NH—;

(vii) —NH—(C═S)—;

(viii) —(C═S)—NH—;

(ix) —NH—;
(x) —NH—(C=O)—NH—;
(xi) —NH—(C=S)—NH—;
(xii) —NH—(C=O)—O—;
(xiii) —O—(C=O)—NH—;
(xiv) —NH—(C=S)—O—;
(xv) —S—(C=O)—NH—;
(xvi) —NH—(C=S)—O—;
(xvii) —NH—(C=S)—S—;
(xviii) —O—(C=S)—NH—;
(xix) —S—(C=S)—NH—;
(xxi) —(C=O)—S—;
(xxii) —O—(C=O)—;
(xxiii) —S—(C=O)—;
(xxiv) —(C=S)—O—;
(xxv) —(C=S)—S—;
(xxvi) —O—(C=S)—;
(xxvii) —S—(C=S)—;
(xxviii) —O—(C=O)—O—;
(xxix) —O—(C=S)—O—; and (G) $R_c$ is an alkyl group, including substituted and unsubstituted alkyl groups, wherein hetero atoms either may or may not be present in the alkyl group;

with the provisos that:

(1) when the compound is of the formula

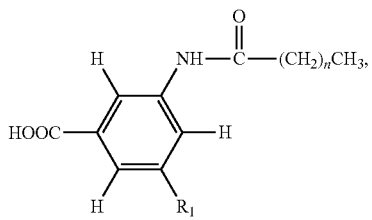

either $R_1$ is not

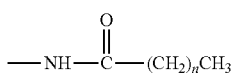

or n is not 9, 10, or 11;

(2) when the compound is of the formula

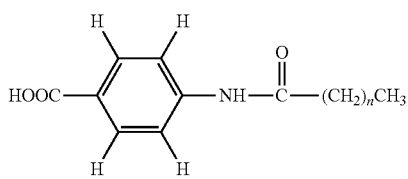

n is not 9, 10, or 11;

(3) when the compound is of the formula

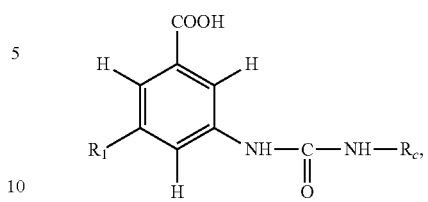

either $R_1$ is not —COOH or $R_c$ is not

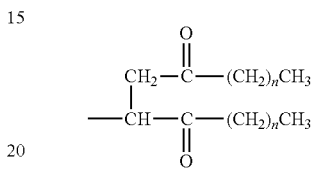

wherein n is 8 to 10; and (4) when the compound is of the formula

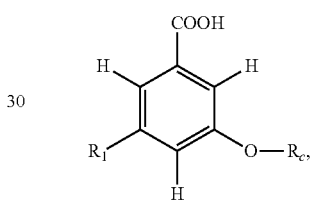

either $R_1$ is not —COOH or $R_c$ is not

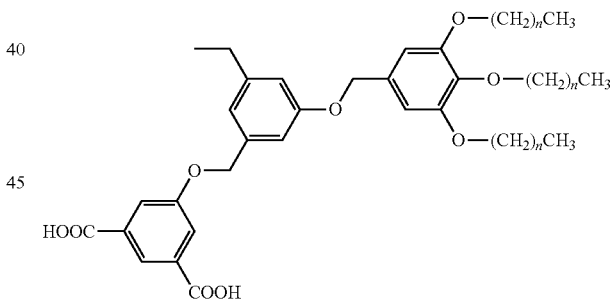

wherein n is from 8 to 10; and wherein alkylated aromatic acid compounds self-assemble in the presence of the organic solvent to form the organogel, wherein the organogel exhibits a gel-to-sol transition temperature of from about 65° C. to about 110° C.

2. A composition according to claim 1 wherein the alkylated aromatic acid compound is present in the organic liquid in an amount of at least about 0.05% by weight.

3. A composition according to claim 1 wherein the alkylated aromatic acid compound is present in the organic liquid in an amount of no more than about 20% by weight.

4. A composition according to claim 1 wherein the organic liquid solvent is a hydrocarbon, an alcohol, an amine, an ester, an ether, a mercaptan, an acid, a sulfone, an anhydride, a siloxane, a polymeric liquid, or a mixture thereof.

5. A composition according to claim 1 wherein the organic liquid solvent is:
(a) a linear, branched, or cyclic unsubstituted aliphatic hydrocarbon;
(b) a linear, branched, or cyclic substituted aliphatic hydrocarbon;
(c) an unsubstituted aromatic or heteroaromatic hydrocarbon;
(d) a substituted aromatic or heteroaromatic hydrocarbon;
(e) a linear, branched, or cyclic unsubstituted aliphatic alcohol;
(e) an aliphatic amine;
(f) an aromatic amine;
(g) an aliphatic ester;
(h) an aromatic ester;
(i) an aliphatic ether;
(j) an aromatic ether; or
(k) a mixture thereof.

6. A composition according to claim 1 wherein exactly one of $R_1$, $R_2$, $R_3$, $R_4$, and $R_5$ is —X—$R_c$.

7. A composition according to claim 1 wherein exactly two of $R_1$, $R_2$, $R_3$, $R_4$, and $R_5$ are each, independently of the other, an —X—$R_c$ group.

8. A composition according to claim 1 wherein exactly one of $R_1$, $R_2$, $R_3$, $R_4$, and $R_5$ is —X—$R_c$ and exactly one of $R_1$, $R_2$, $R_3$, $R_4$, and $R_5$ is —COOH.

9. A composition according to claim 1 wherein the alkylated aromatic acid is of the formula

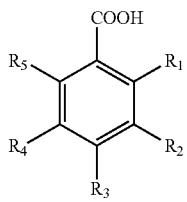

or mixtures thereof, $R_1$, $R_3$, and $R_5$ are each hydrogen atoms, $R_2$ is —$X_1$—$R_{c1}$, and $R_4$ is —COOH or —$X_2$—$R_{c2}$, wherein $X_1$ and $X_2$ have the same definition as X and can be either the same as or different from each other and $R_{c1}$ and $R_{c2}$ have the same definition as $R_c$ and can be either the same as or different from each other.

10. A composition according to claim 1 wherein $R_c$ is:
(a) a linear unsubstituted alkyl group of the formula —$(CH_2)_n CH_3$, wherein n is an integer,
(b) a branched unsubstituted alkyl group of the formula

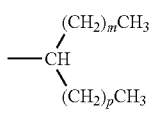

wherein m is an integer and p is an integer;
(c) a branched unsubstituted alkyl group of the formula

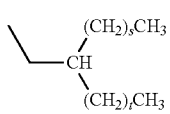

wherein s is an integer and t is an integer;
(d) a branched unsubstituted alkyl group of the formula

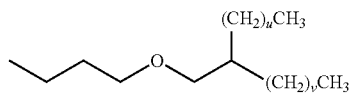

wherein u is an integer and v is an integer; or
(e) a multi-branched unsubstituted alkyl group of the formula

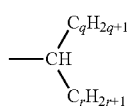

wherein q is an integer and r is an integer.

11. A composition according to claim 1 wherein the alkylated aromatic acid is

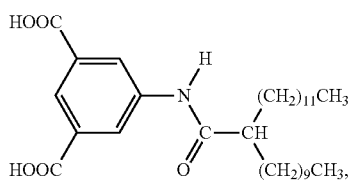

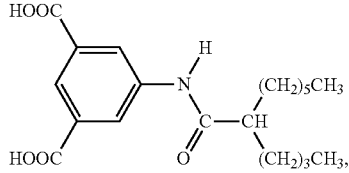

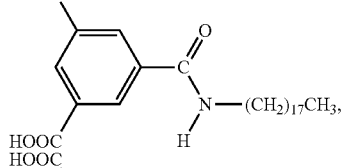

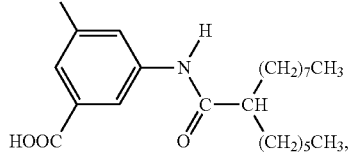

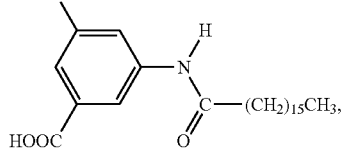

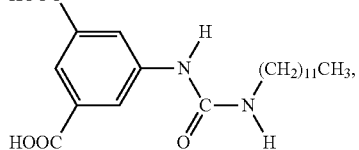

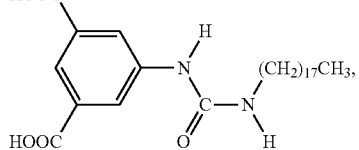

-continued

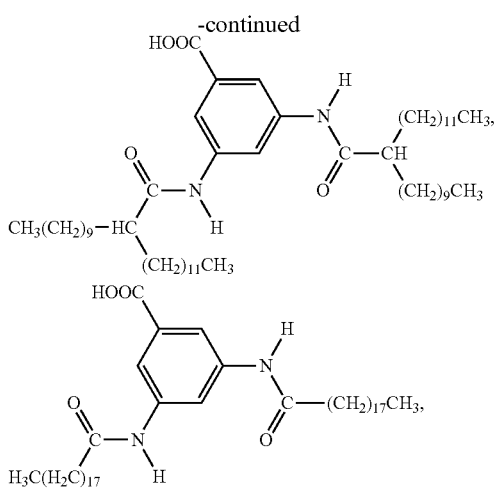

12. A composition according to claim 1 wherein:
(a) the alkylated aromatic acid compound is present in the organic liquid in an amount of no more than about 5% by weight; and
(b) the organogel exhibits a gel-to-sol transition temperature of from about 65° C. to about 110° C.

13. A composition according to claim 12 wherein the alkylated aromatic acid compound is present in the organic liquid in an amount of no more than about 1% by weight.

14. A composition comprising an organogel consisting of a) an alkylated aromatic acid and b) an organic liquid solvent entrapped within the organogel wherein the liquid is rigidified:
wherein the alkylated aromatic acid compound is of the formula

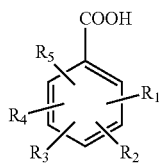

or mixtures thereof, wherein $R_1$, $R_2$, $R_3$, $R_4$, and $R_5$ each, independently of the other, is:
(A) hydrogen atoms;
(B) alkyl groups, including substituted and unsubstituted alkyl groups, wherein hetero atoms either may or may not be present in the alkyl group;
(C) aryl groups, including substituted and unsubstituted aryl groups, wherein hetero atoms either may or may not be present in the aryl group;
(D) arylalkyl groups, including substituted and unsubstituted arylalkyl groups, wherein hetero atoms either may or may not be present in either or both of the alkyl portion and the aryl portion of the arylalkyl group; or
(E) alkylaryl groups, including substituted and unsubstituted alkylaryl groups, wherein hetero atoms either may or may not be present in either or both of the alkyl portion and the aryl portion of the alkylaryl group;
provided that at least one of $R_1$, $R_2$, $R_3$, $R_1$, and $R_5$ is —X—$R_c$, wherein:
(F) —X— is a linking group between $R_c$ and the aromatic group, wherein —X— is selected from the group consisting of (i) —O—;
(ii) —S—;
(iii) —SO—;
(iv) —SO$_2$—;
(v) —NH—(C=O)—;
(vi) —(C=O)—NH—;
(vii) —NH—(C=S)—;
(viii) —(C=S)—NH—;
(ix) —NH—;
(x) —NH—(C=O)—NH—;
(xi) —NH—(C=S)—NH—;
(xii) —NH—(C=O)—O—;
(xiii) —O—(C=O)—NH—;
(xiv) —NH—(C=S)—O—;
(xv) —S—(C=O)—NH—;
(xvi) —NH—(C=S)—O—;
(xvii) —NH—(C=S)—S—;
(xviii) —O—(C=S)—NH—;
(xix) —S—(C=S)—NH—;
(xxi) —(C=O)—S—;
(xxii) —O—(C=O)—;
(xxiii) —S—(C=O)—;
(xxiv) —(C=S)—O—;
(xxv) —(C=S)—S—;
(xxvi) —O—(C=S)—;
(xxvii) —S—(C=S)—;
(xxviii) —O—(C=O)—O—;
(xxix) —O—(C=S)—O—; and
(G) $R_c$ is an alkyl group, including substituted and unsubstituted alkyl groups, wherein hetero atoms either may or may not be present in the alkyl group;
with the provisos that:
(1) when the compound is of the formula

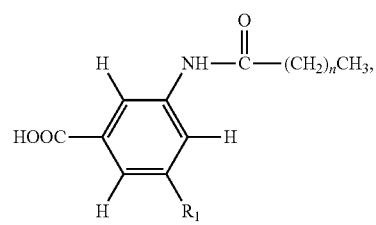

either $R_1$ is not

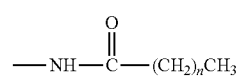

or n is not 9, 10, or 11;
(2) when the compound is of the formula

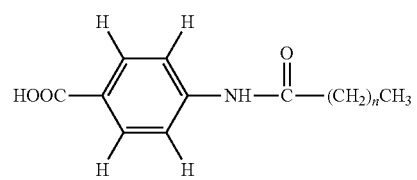

n is not 9, 0, or 11;

(3) when the compound is of the formula

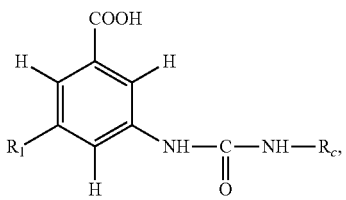

either $R_1$ is not —COOH or $R_c$ is not

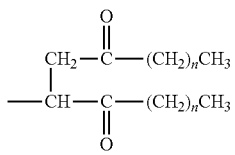

wherein n is 8 to 10; and (4) when the compound is of the formula

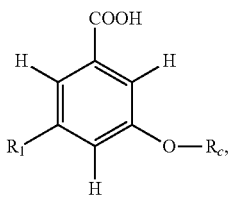

either $R_1$ is not —COOH or $R_c$ is not

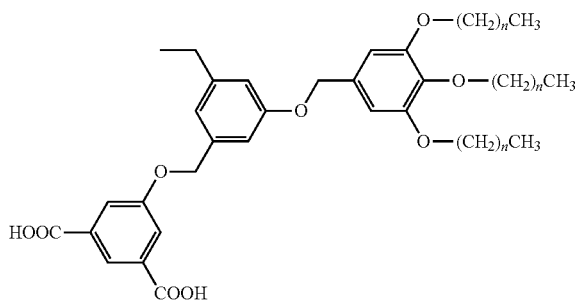

wherein n is from 8 to 10;

wherein the alkylated aromatic acid compound is present in the organic liquid in an amount of no more than about 5% by weight;

wherein the organogel exhibits a gel-to-sol transition temperature of from about 65° C. to about 110° C.; and wherein alkylated aromatic acid compounds self-assemble in the presence of the organic solvent to form the organogel.

15. A composition comprising an organogel consisting of a) an alkylated aromatic acid and b) an organic liquid solvent entrapped within the organogel wherein the liquid is rigidified:

wherein the alkylated aromatic acid compound is of the formula

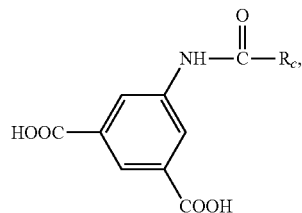

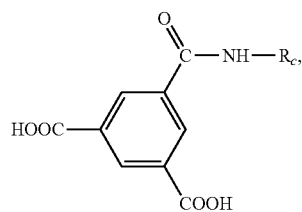

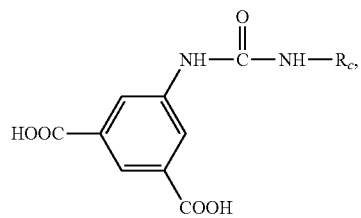

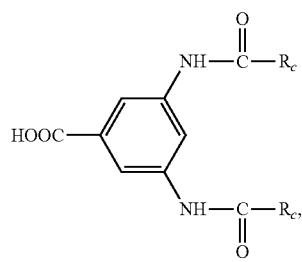

or mixtures thereof, wherein $R_c$ is:

(i) a linear unsubstituted alkyl group of the formula —$(CH_2)_n CH_3$, wherein n is an integer;

(ii) a branched unsubstituted alkyl group of the formula

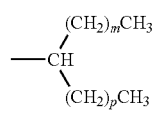

wherein m is an integer and p is an integer;

(iii) a branched unsubstituted alkyl group of the formula

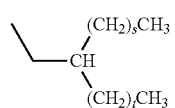

wherein s is an integer and t is an integer;

(iv) a branched unsubstituted alkyl group of the formula

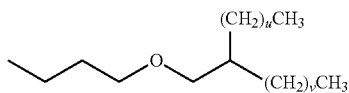

wherein u is an integer and v is an integer;

(v) a multi-branched unsubstituted alkyl group of the formula

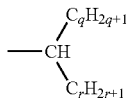

wherein q is an integer and r is an integer;
or mixtures thereof; with the proviso that when the compound is of the formula

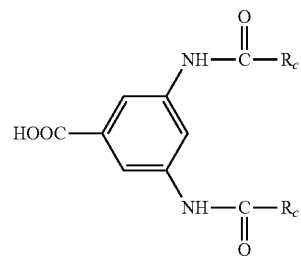

and $R_c$ is a linear unsubstituted alkyl group of the formula $-(CH_2)_n CH_3$, n is not 9, 10, or 11, wherein the organogel exhibits a gel-to-sol transition temperature of from about 65° C. to about 110° C.

16. A composition according to claim 15 wherein:
(a) the alkylated aromatic acid compound is present in the organic liquid in an amount of no more than about 5% by weight.

* * * * *